United States Patent [19]
Heath et al.

[11] Patent Number: 5,407,958
[45] Date of Patent: Apr. 18, 1995

[54] THERAPEUTIC SKIN COMPOSITION

[75] Inventors: Jinger L. Heath, Dallas; Clifton R. Sanders, Plano; John H. Murphy, Double Oak; Rhonda Atkins, Duncanville, all of Tex.

[73] Assignee: BeautiControl Cosmetics, Inc., Carrollton, Tex.

[21] Appl. No.: 99,855

[22] Filed: Jul. 30, 1993

[51] Int. Cl.[6] .................. A61K 31/22; A61K 31/225
[52] U.S. Cl. .................. 514/546; 514/547; 514/947
[58] Field of Search .............. 424/28.06; 514/546, 514/547, 947

[56] References Cited

U.S. PATENT DOCUMENTS

| | | | |
|---|---|---|---|
| 2,118,566 | 3/1938 | De Wayne | 424/601 |
| 2,717,850 | 9/1955 | Schmitz | 252/106 |
| 3,068,145 | 12/1962 | Glenn | 514/171 |
| 3,096,244 | 7/1963 | Ehrhart | 514/625 |
| 3,124,506 | 3/1964 | Holman | 424/55 |
| 3,259,545 | 7/1966 | Teller | 424/66 |
| 3,549,544 | 12/1970 | Johnson | 252/545 |
| 3,608,086 | 9/1971 | Halpern | 514/557 |
| 3,639,623 | 2/1972 | Ritschel et al. | 514/530 |
| 3,640,883 | 2/1972 | Gotte | 252/545 |
| 3,666,863 | 5/1972 | Swanbeck | 514/554 |
| 3,806,593 | 4/1974 | Swanbeck et al. | 424/401 |
| 3,879,537 | 4/1975 | Van Scott et al. | 514/460 |
| 3,920,835 | 11/1975 | Van Scott et al. | 514/460 |
| 3,984,566 | 10/1976 | Van Scott et al. | 514/460 |
| 3,988,470 | 10/1976 | Van Scott et al. | 514/451 |
| 4,021,572 | 5/1977 | Van Scott et al. | 514/557 |
| 4,105,782 | 8/1978 | Yu et al. | 514/613 |
| 4,105,783 | 8/1978 | Yr et al. | 514/352 |
| 4,178,373 | 12/1979 | Klein et al. | 514/1 |
| 4,197,316 | 4/1980 | Yu et al. | 514/554 |
| 4,203,969 | 5/1980 | Yarrow et al. | 514/732 |
| 4,224,339 | 9/1980 | Van Scott et al. | 514/553 |
| 4,234,599 | 11/1980 | Van Scott et al. | 514/451 |
| 4,246,261 | 1/1981 | Van Scott et al. | 514/171 |
| 4,283,386 | 8/1981 | Van Scott et al. | 424/70 |
| 4,287,214 | 9/1981 | Van Scott et al. | 514/732 |
| 4,316,902 | 2/1982 | Yu et al. | 514/352 |
| 4,363,815 | 12/1982 | Yu et al. | 139/57 |
| 4,380,549 | 4/1983 | Van Scott et al. | 514/23 |
| 4,518,789 | 5/1985 | Yu et al. | 560/105 |
| 4,542,129 | 9/1985 | Orentreich | 514/178 |
| 4,588,590 | 5/1986 | Bernstein | 424/195.1 |
| 4,595,591 | 6/1986 | Mardi et al. | 424/718 |
| 4,774,255 | 9/1988 | Black et al. | 514/423 |
| 4,837,019 | 6/1989 | Georgalas et al. | 424/78.06 |
| 4,946,832 | 8/1990 | Goode et al. | 514/53 |
| 5,091,171 | 2/1992 | Yu et al. | 424/642 |
| 5,093,360 | 3/1992 | Yu et al. | 514/463 |
| 5,153,230 | 10/1992 | Jaffery | 514/847 |
| 5,158,762 | 10/1992 | Pierce | 424/47 |

FOREIGN PATENT DOCUMENTS 89013685 1/1989 Japan.
WO18116 10/1992 WIPO.

OTHER PUBLICATIONS

Neil A. Fenske, MD and Sharon E. Albers, MD Sep. 9, 1990 pp. 59–67; Geriatrics Cosmetic modalities for aging skin: What to tell patients.

Lawrence S. Moy, MD, Howard Murad, MD, Ronald L. Moy, MD; 1993 J Dermatol Surg Oncol; Glycolic Acid Peels for the Treatment of Wrinkles and Photoaging pp. 243–246.

Mark C. Dahl, MD. and Arlene C. Dahl: vol. 119, Jan. 1983; Arch Dermatol 12% Lactate Lotion for the Treatment of Xerosis A Double-blind Clinical Evaluation pp. 27–30.

Primary Examiner—Raymond Henley, III
Assistant Examiner—K. Weddington
Attorney, Agent, or Firm—Warren B. Kice

[57] ABSTRACT

Therapeutic and preventive compositions that treat dull, dry and rough skin, improve skin smoothness and elasticity, diminish fine lines and wrinkles, prevent acne and promote renewed skin vibrance. The compositions include an alpha hydroxy acid and a preservative.

5 Claims, No Drawings

THERAPEUTIC SKIN COMPOSITION

FIELD OF THE INVENTION

The present invention relates generally to topical applications for human skin conditions and more specifically to therapeutic and preventive compositions that treat dull, dry and rough skin, exfoliate skin, improve skin smoothness and elasticity, diminish fine lines and wrinkles, prevent acne and promote renewed skin vibrance.

BACKGROUND OF THE INVENTION

It is well known in the art that alpha hydroxy acids are useful in the treatment of various skin maladies such as dry skin, ichthyosis, eczema, palmar keratoses, plantar keratoses, dandruff, acne, warts, herpes, pruritis, psoriasis, age spots, wrinkles and disturbed keratinization. Repeated application of topical formulations including alpha hydroxy acids, however, has undesirably resulted in mild to sometimes severe skin irritation. The cause of the skin irritation is likely attributable to a lowering of the pH of the skin. As mentioned in U.S. Pat. No. 5,091,171 to Yu et al., the upper layers of normal skin have a pH of 4.2 to 5.6 while the compositions containing alpha hydroxy acids typically have a pH of less than 3.0. Repeated topical application of such compositions can cause a decrease in the pH of the skin. Various attempts have been made to overcome this drawback of alpha hydroxy acids but such attempts largely have been unsuccessful. For instance, the alpha hydroxy acids have been reacted with organic primary, secondary or tertiary alkylamines, alkanol amines, diamines, dialkylamines, dialkanolamines, alkylalkanolamines, trialkylamines, trialkanolamines, dialkyl alkanolamines and alkyl dialkanolamines. For instance, see U.S. Pat. Nos. 4,234,599, 4,197,316, 4,021,572, 4,105,782 and 4,105,783. The products of such reactions, however, lose most of their therapeutic effects, probably because the penetration and distribution of the active ingredient to the target site in the skin is greatly diminished.

SUMMARY OF THE INVENTION

The foregoing problems are solved and a technical advance is achieved by therapeutic skin compositions comprising an alpha hydroxy acid and a preservative comprising sodium hydroxymethylglycinate.

In preferred embodiments, the compositions include one or more alpha hydroxy acids selected from glycolic acid, citric acid, lactic acid, malic acid, tartronic acid, tartaric acid and glucuronic acid.

In other preferred embodiments, the compositions include one or more alpha hydroxy acids selected from citric acid, lactic acid and tartaric acid.

The compositions of the present invention are provided in a cream base that also includes additional preservatives to increase the shelf life of the compositions.

A technical advantage achieved with compositions of the present invention is that the compositions treat dull, dry and rough skin, exfoliate skin, improve skin smoothness and elasticity, diminish fine lines and wrinkles, prevent acne and promote renewed skin vibrance without the concomitant skin irritation associated with other alpha hydroxy acid compositions.

DESCRIPTION OF THE PREFERRED EMBODIMENTS

The composition of the present invention comprises one or more alpha hydroxy acids selected from glycolic acid, citric acid, lactic acid, malic acid, tartronic acid, tartaric acid and glucuronic acid. Preferably, the compositions include one or more alpha hydroxy acids selected from citric acid, lactic acid and tartaric acid. In a preferred embodiment, the composition includes a triple alpha hydroxy acid complex including lactic acid, citric acid and tartaric acid in a concentration of from about 0.05 weight % up to about 15.00 weight % and a concentration of from about 0.01 weight % up to about 15.00 weight % of a composition comprising about 28.00 weight % to about 35.00 weight % of lactic acid.

A suitable source of a triple alpha hydroxy acid complex including lactic acid, citric acid and tartaric acid is sold under the trademark Lemon/Passion Fruit Complex ™ which is commercially available from Centerchem.

A suitable source of a composition comprising about 28.00 weight % to about 35.00 weight % of lactic acid is sold under the trademark Biolac ™ which consists of about 28.00 weight % to about 35.00 weight % of lactic acid and about 65.00 weight % to about 72.00 weight % of inert ingredients and is commercially available from Barnet Products.

Sodium hydroxymethylglycinate is provided in the composition to neutralize the alpha hydroxy acid and reduce skin irritation. The sodium hydroxymethylglycinate may be provided in a concentration of from about 0.20 weight % to about 1.50 weight %.

A suitable source of sodium hydroxymethylglycinate is sold under the trademark Suttocide A ® which is commercially available from Sutton Labs, a division of ISP Technology Inc.

Although a simple solution of the alpha hydroxy acids and the sodium hydroxymethylglycinate in water is effective as a skin treating composition according to the present invention, various well known and conventional topical cosmetic carriers such as suspending agents, thickeners, humectants, preservatives, emollients, emulsifiers, film formers and fragrant oils are provided for cosmetic effects and/or to improve the physical consistency of the formulation and to serve as a diluent for the alpha hydroxy acids and the sodium hydroxymethylglycinate.

The compositions of the present invention may include a suspending agent such as magnesium aluminum silicate in a concentration of from about 0.20 weight % to about 2.00 weight %. A suitable source of magnesium aluminum silicate is sold under the trademark Veegum ® which is commercially available from R. T. Vanderbilt Company, Inc.

The compositions of the present invention may include one or more thickeners such as hydroxyethylcellulose in a concentration of from about 0.05 weight % to about 0.50 weight %, xanthan gum in a concentration of from about 0.01 weight % to about 0.70 weight % and stearyl alcohol in a concentration of from about 0.50 weight % to about 5.00 weight %. A suitable source of hydroxyethylcellulose is sold under the trademark Natrosol ® 250 which is commercially available from Aqualon Company. A suitable source of xanthan gum is sold under the trademark Keltrol ® which is commercially available from Kelco. A suitable source of stearyl alcohol is commercially available from Sherex Chemical Company.

The compositions of the present invention may include a humectant such as propylene glycol U.S. Patent in a concentration of from about 1.00 weight % to about 8.00 weight %. A suitable source of propylene glycol U.S. Patent is B.A.S.F.

The compositions of the present invention may include one or more preservatives such as phenoxyethanol in a concentration of from about 0.01 weight % to about 0.50 weight % and benzyl alcohol in a concentration of from about 0.01 weight % to about 1.00 weight %. A suitable source of phenoxyethanol is sold under the trademark Phenoxetol ® which is commercially available from Nipa Laboratories, Ltd. Benzyl alcohol is commercially available from Creative Fragrances. The preservatives are provided to improve the shelf life of the compositions.

The compositions of the present invention may include one or more emollients such as caprylic/capric triglyceride in a concentration of from about 1.00 weight % to about 12.00 weight % isopropyl palmitate in a concentration of from about 1.00 weight % to about 10.00 weight %, dimethicone in a concentration of from about 0.10 weight % to about 4.00 weight %, a branched chain hydrocarbon obtained by hydrogenation of shark liver oil or other natural oils in a concentration of from about 1.00 weight % to about 6.00 weight % and cyclomethicone which is a cyclic dimethyl polysiloxane compound in a concentration of from about 1.00 weight % to about 6.00 weight %. A suitable source of caprylic/capric triglyceride is sold under the trademark Myritol ® 318 which is commercially available from Caschem Inc. A suitable source of isopropyl palmitate is sold under the trademark Wickenol ® 111 which is commercially available from Wickhen Products, Inc. A suitable source of dimethicone is sold under the trademark Dow Corning ® 225 Fluid which is a mixture of fully methylated linear siloxane polymers and blocked with trimethyl siloxane units and which is commercially available from Dow Corning Corporation. A suitable source of a branched chain hydrocarbon obtained by hydrogenation of shark liver oil or other natural oils is sold under the trademark Squalane TM which is commercially available from Robeco Chemical. A suitable source of cyclomethicone is commercially available from Dow Corning Corporation.

The compositions of the present invention may include one or more emulsifiers such as stearic acid in a concentration of from about 1.00 weight % to about 10.00 weight %, glyceryl stearate/polyethylene glycol 100 stearate in a concentration of from about 2.50 weight % to about 10.00 weight %, cetyl alcohol in a concentration of from about 0.20 weight % to about 4.00 weight %, sorbitan stearate in a concentration of from about 0.20 weight % to about 2.00 weight % and stearyl alcohol and ceteareth-20 in a concentration of from about 0.50 weight % to about 9.00 weight %. A suitable source of stearic acid is sold under the trademark Emersol ® 132 which is commercially available from Henkel Corporation. A suitable source of glyceryl stearate/polyethylene glycol 100 stearate is sold under the trademark Lipomulse 165 TM which is commercially available from Lipo Chemicals. A suitable source of cetyl alcohol is sold under the trademark Adol ® 52 which is commercially available from Sherex Chemical Company. A suitable source of sorbitan stearate is sold under the trademark Liposorb S TM which is commercially available from Lipo Chemicals. A suitable source of stearyl alcohol and ceteareth-20 is sold under the trademark Promulgen G TM which is commercially available from Amerchol.

The compositions of the present invention may include a film former such as a mixture of liquid hydroxyl terminated polymers and polyethylene glycol in a concentration of from about 1.00 weight % to about 5.00 weight %. A suitable source of a mixture of liquid hydroxyl terminated polymers and polyethylene glycol is sold under the trademark Polyolprepolymer-2 TM which is commercially available from Barnet Products.

The compositions of the present invention may include one or more fragrant oils such as almond oil in a concentration of from about 0.01 weight % to about 0.30 weight % and jasmine oil in a concentration of from about 0.01 weight % to about 0.50 weight %. Almond Oil is commercially available from Creative Fragrances. A suitable source of sold under the trademark jasmine oil is Jasmine Oil 1524-A which is commercially available from Creative Fragrances.

Deionized water may be provided in the compositions of the present invention as an inert carrier which acts as a diluent and which also has some moisturizing properties.

It is understood that the compositions of the present invention may include other conventional and well known topical cosmetic carriers such as suspending agents, thickeners, humectants, preservatives, emollients, emulsifiers, film formers and fragrant oils. It is also understood that the specifically enumerated cosmetic carriers may be freely substituted with other conventional and well known carriers to achieve a desired texture and lubricity of the compositions.

The present invention will now be described in more detail with reference to the following examples. These examples are merely illustrative of the compositions and methods of the present invention and are not intended to be limiting.

| Phase | Face and Neck Creme Material (Trademark) | % by Wt. |
| --- | --- | --- |
| A | Deionized Water | 54.09 |
|   | magnesium aluminum silicate (Veegum ®) | 0.80 |
|   | hydroxyethylcellulose (Natrosol ® 250) | 0.20 |
|   | Propylene Glycol U.S.P. | 5.00 |
|   | phenoxyethanol (Phenoxetol ®) | 0.30 |
|   | Benzyl Alcohol | 0.50 |
| B | caprylic/capric triglyceride (Myritol ® 318) | 8.00 |
|   | stearic acid (Emersol ® 132) | 5.00 |
|   | isopropyl palmitate (Wickenoll ® 111) | 5.80 |
|   | glyceryl stearate/polyethylene glycol 100 stearate (Lipomulse 165 TM) | 7.00 |
|   | cetyl alocohol (Adol ® 52) | 0.60 |
|   | sorbitan stearate (Liposorb S TM) | 0.50 |
|   | dimethicone (Dow Corning ® 225 Fluid) | 1.30 |
| C | lactic acid (Biolac TM) | 10.00 |
|   | triple alpha hydroxy acid (Lemon-Passion Fruit Complex TM) | 0.10 |
| D | sodium hydroxymethylglycinate (Suttocide A ®) | 0.75 |
| E | Almond Oil | 0.03 |
|   | jasmine oil (Jasmine Oil 1524-A TM) | 0.03 |
|   | TOTAL | 100.00 |

The "magnesium aluminum silicate sold under the trademark" Veegum ® and "hydroxyethylcellulose sold under the trademark" Natrosol ® 250 were combined and sifted into the deionized water with high speed mixing in a stainless steel mixing vessel sold under the trademark Lee TM Kettle equipped with a propeller-type mixer sold under the trademark Lightnin TM. Mixing was continued until an adequately dispersed homogeneous solution was obtained then the propylene glycol was added and the solution was heated to 78° C. When the solution reached a temperature of 78° C. the remainder of the Phase A ingredients were added. The Phase B ingredients were mixed in a side vessel and heated to 80° C. When the Phase A and B solutions reached temperatures of 78° C. and 80° C., respectively, the Phase B solution was added to the Phase A solution and the resultant solution was mixed well until an adequately dispersed homogeneous solution was obtained. The temperature of the solution was then maintained at 75° C. for 10 minutes with mixing. After the expiration of the 10 minute period, the solution was cooled to 40° C. When the solution reached 40° C., Phase C was added and the resultant mixture was mixed well until an adequately dispersed homogeneous solution was obtained. This mixture was cooled to 35° C. at which point Phase D was added. The resultant mixture was mixed well until an adequately dispersed homogeneous mixture was obtained. Finally the composition was cooled to 30° C. When the mixture reached 30° C., Phase E was added and the resultant mixture was mixed well until an adequately dispersed homogeneous mixture was obtained.

Clinical trials were conducted to evaluate the changes in human skin condition as a consequence of the topical application of the composition prepared according to this example. According to the clinical trials, 30 panelists were assigned to Group A which received the product of Example 1 while 28 panelists were assigned to Group B which received a placebo. The Group A and Group B panelists were examined after 2 weeks and after 4 weeks of usage of the product of Example 1 and the placebo, respectively. All 30 of the Group A panelists and all 28 of the Group B panelists were examined after 2 weeks while 21 of the Group A panelists and 16 of the Group B panelists were examined after 4 weeks. Table A below shows the results of such examinations. The percentages indicated in Table A for panelists showing improvement after 4 weeks were based on the actual number of panelists examined after 4 weeks of usage of the product of Example 1 or the placebo rather than the total number of panelists in Group A or Group B, respectively.

TABLE A

The Percentage of Panelists Showing Improvement Following Two and Four Weeks of Usage

| Skin Changes | GROUP A N = 30 two weeks | GROUP A N = 21 four weeks | GROUP B N = 28 two weeks | GROUP B N = 16 four weeks |
|---|---|---|---|---|
| reduced roughness | NC* | 15% | 3.6% | NC |
| firmness | NC | NC | NC | NC |
| reduced hyperpigmentation | 36.7% | 52.6% | 25% | 6.2% |
| reduced appearance of fine lines | 90% | 100% | 42.9% | 6.2% |
| reduced appearance of major lines | 13% | 31% | 5.6% | 6.2% |
| reduced dryness | 36.7% | 36.8% | 25% | 12.5% |
| sallowness | 6.7% | 10% | 7.1% | NC |

*No change

The results of the clinical trials demonstrate significant positive changes in skin condition in terms of reduced roughness, reduced hyperpigmentation, reduced appearance of fine lines, reduced appearance of major lines and reduced dryness for those panelists receiving the composition according to example 1 when compared to those panelists receiving the placebo composition.

| Phase | Hand and Body Creme Material (Trademark) | % by Wt. |
|---|---|---|
| A | Deionized Water | 54.09 |
| | magnesium aluminum silicate (Veegum ®) | 0.80 |
| | hydroxyethylcellulose (Natrosol ® 250) | 0.20 |
| | Propylene Glycol U.S.P. | 5.00 |
| | phenoxyethanol (Phenoxetol ®) | 0.30 |
| | Benzyl Alcohol | 0.50 |
| B | caprylic/capric triglyceride (Myritol ® 318) | 8.00 |
| | stearic acid (Emersol ® 132) | 6.00 |
| | isopropyl palmitate (Wickenol ® 111) | 5.00 |
| | glyceryl stearate/polyethylene glycol 100 stearate (Lipomulse 165 TM) | 7.00 |
| | cetyl alcohol (Adol ® 52) | 0.80 |
| | sorbitan stearate (Liposorb S TM) | 0.50 |
| | dimethicone (Dow Corning ® 225 Fluid) | 1.00 |
| C | triple alpha hydroxy acid (Lemon-Passion Fruit Complex TM) | 10.00 |
| D | sodium hydroxymethylglycinate (Suttocide A ®) | 0.75 |
| E | Almond Oil | 0.03 |
| | jasmine oil (Jasmine Oil 1524-A TM) | 0.03 |
| | TOTAL | 100.00 |

The "magnesium aluminum silicate sold under the trademark" Veegum ® and "hydroxyethylcellulose sold under the trademark" Natrosol ® 250 were combined and sifted into the deionized water with high speed mixing in a stainless steel mixing vessel sold under the trademark Lee TM Kettle equipped with a propeller-type mixer sold under the trademark Lightnin TM. Mixing was continued until an adequately dispersed homogeneous solution was obtained then the propylene glycol was added and the solution was heated to 78° C. When the solution reached a temperature of 78° C. the remainder of the Phase A ingredients were added. The Phase B ingredients were mixed in a side vessel and heated to 80° C. When the Phase A and B solutions reached temperatures of 78° C. and 80° C., respectively, the Phase B solution was added to the Phase A solution and the resultant solution was mixed well until an adequately dispersed homogeneous solution was obtained. The temperature of the solution was then maintained at 75° C. for 10 minutes with mixing. After the expiration of the 10 minute period, the solution was cooled to 40° C. When the solution reached 40° C., Phase C was added and the resultant mixture was mixed well until an adequately dispersed homogeneous solution was obtained. This mixture was cooled to 35° C. at which point Phase D was added. The resultant mixture was mixed well until an adequately dispersed homogeneous mixture was obtained. Finally the composition was cooled to 30° C. When the mixture reached 30° C., Phase E was added and the resultant mixture was mixed well until an adequately dispersed homogeneous mixture was obtained.

Clinical trials were conducted to evaluate the changes in human skin condition as a consequence of the topical application of the composition prepared according to this example. According to the clinical trials, 32 panelists were assigned to Group A which received the product of Example 2 while 28 panelists were assigned to Group B which received a placebo. The Group A and Group B panelists were examined after 2 weeks and after 4 weeks of usage of the product of Example 2 and the placebo, respectively. All 32 of the Group A panelists and all 28 of the Group B panelists were examined after 2 weeks while 21 of the Group A panelists and 16 of the Group B panelists were examined after 4 weeks. Table B below shows the results of such examinations. The percentages indicated in Table B for panelists showing improvement after 4 weeks were based on the actual number of panelists examined after 4 weeks of usage of the product of Example 2 or the placebo rather than the total number of panelists in Group A or Group B, respectively.

TABLE B

The Percentage of Panelists Showing Improvement Following Two and Four Weeks of Usage

| Skin Changes | GROUP A | | GROUP B | |
|---|---|---|---|---|
| | N = 32 two weeks | N = 21 four weeks | N = 28 two weeks | N = 16 four weeks |
| reduced roughness | 25% | 14.3% | 3.6% | NC |
| firmness | NC | NC | NC | NC |
| reduced hyperpigmentation | 46% | 57% | 25% | 6.2% |
| reduced appearance of fine lines | 81% | 90% | 42.9% | 6.2% |
| reduced appearance of major lines | 31.3% | 28.6% | 5.6% | 6.2% |
| reduced dryness | 31.3% | 33.3% | 25% | 12.5% |
| sallowness | 15.6% | 9.6% | 7.1% | NC |

*No change

The results of the clinical trials demonstrate significant positive changes in skin condition in terms of reduced roughness, reduced hyperpigmentation, reduced appearance of fine lines, reduced appearance of major lines and reduced dryness for those panelists receiving the composition according to example 2 when compared to those panelists receiving the placebo composition.

7% lactic Acid Creme

| Seg. | Material (Trademark) | % by Wt. | Grams |
|---|---|---|---|
| A | Deionized Water | 62.60 | 313.00 |
| | Propylene Glycol U.S.P. | 4.00 | 20.00 |
| | Xanthan Gum | 0.50 | 2.50 |
| | phenoxyethanol (Phenoxetol ®) | 0.30 | 1.50 |
| | Benzyl Alcohol | 0.50 | 2.50 |
| B | branched chain hydrocarbon (Squalane TM) | 4.00 | 20.00 |
| | hdyroxyl terminated polymers/ polyethylene glycol (Polyolprepolymer-2 TM) | 3.00 | 15.00 |
| | caprylic/capric triglyceride (Myritol ® 318) | 5.00 | 25.00 |
| | stearic acid (Emersol ® 132) | 3.20 | 16.00 |
| | Cyclomethicone | 4.00 | 20.00 |
| | dimethicone (Dow Corning ® 225 Fluid) | 1.00 | 5.00 |
| | Promulgen G TM | 1.85 | 9.25 |
| | glyceryl stearate/polyethylene glycol 100 stearate (Lipomulse 165 TM) | 2.30 | 11.50 |
| C | lactic acid (Biolac TM) | 7.00 | 35.00 |
| D | sodium hydroxymethylglycinate (Suttocide A ®) | 0.75 | 3.75 |
| | TOTAL | | 500.00 |

The xanthan gum was sifted into the deionized water with high speed mixing in a stainless steel mixing vessel sold under the trademark Lee TM Kettle equipped with a propeller-type sold under the trademark Lightnin TM mixer. Mixing was continued until an adequately dispersed homogeneous solution was obtained and then the remainder of the Phase A ingredients were added. This mixture was heated to 75° C. The Phase B ingredients were mixed in a side vessel and heated to 75° C. When the Phase A and B solutions reached a temperature of 75° C., the Phase B solution was added to the Phase A solution and the resultant solution was mixed well until an adequately dispersed homogeneous solution was obtained. The temperature of the solution was then maintained at 70° C. for 10 minutes with mixing. After the expiration of the 10 minute period, the solution was cooled to 40° C. When the solution reached 40° C., Phase C was added and the resultant mixture was mixed well until an adequately dispersed homogeneous solution was obtained. This mixture was cooled to 35° C. at which point Phase D was added. The resultant mixture was mixed well until an adequately dispersed homogeneous mixture was obtained. Finally the composition was cooled to 30° C.

EXAMPLE 4

15% Lactic Acid Creme

| Seg. | Material (Trademark) | % by Wt. | Grams |
|---|---|---|---|
| A | Deionized Water | 50.05 | 1501.50 |
| | phenoxyethanol (Phenoxetol ®) | 0.30 | 9.00 |
| | Benzyl Alcohol | 0.50 | 15.00 |
| | Propylene Glycol U.S.P. | 4.00 | 120.00 |
| | Xanthan Gum | 0.80 | 14.00 |
| B | cetyl alcohol (Adol ® 52) | 2.00 | 60.00 |
| | branched chain hydrocarbon (Squalane TM) | 4.00 | 120.00 |
| | hydroxyl terminated polymers/ polyethylene glycol (Polyolprepolymer-2 TM) | 3.00 | 90.00 |
| | caprylic/capric triglyceride (Myritol ® 318) | 5.00 | 150.00 |
| | stearic acid (Emersol ® 132) | 3.80 | 114.00 |
| | Cyclomethicone | 4.00 | 120.00 |
| | dimethicone (Dow Corning ® 225 Fluid) | 1.20 | 36.00 |
| | stearyl alcohol/ceteareth-20 (Promulgen G TM) | 2.30 | 69.00 |
| | glyceryl stearate/polyethylene glycol 100 stearate (Lipomulse 165 TM) | 2.50 | 75.00 |
| | Stearyl Alcohol | 0.80 | 24.00 |
| C | lactic acid (Biolac TM) | 15.00 | 450.00 |
| | sodium hydroxymethylglycinate (Suttocide A ®) | 0.75 | 22.50 |
| | TOTAL | | 3000.00 |

The deionized water was heated to 80° C. and the phenoxyethanol and the benzyl alcohol were added to the deionized water and mixed at high speed in a stainless steel mixing vessel sold under the trademark Lee TM Kettle equipped with a propeller-type sold under the trademark Lightnin mixer. Mixing was continued until an adequately dispersed homogeneous solution was obtained and then the remainder of the Phase A ingredients were added. This mixture was heated to 75° C. The Phase B ingredients were mixed in a side vessel and heated to 75° C. When the Phase A and B solutions reached a temperature of 75° C., the Phase B solution was added to the Phase A solution and the resultant solution was mixed well until an adequately dispersed homogeneous solution was obtained. The temperature of the solution was then maintained at 70° C. for 10 minutes with mixing. After the expiration of the 10 minute period, the solution was cooled to 40° C. When the solution reached 40° C., Phase C was added and the resultant mixture was mixed well until an adequately dispersed homogeneous solution was obtained. This mixture was cooled to 35° C. at which point Phase D was added. The resultant mixture was mixed well until an adequately dispersed homogeneous mixture was obtained. Finally the composition was cooled to 30° C.

EXAMPLE 5

Neutralization of Alpha Hydroxy Acids

BIOLAC TM BRANK LACTIC NEUTRALIZATION:

To 3.30 grams of Lactic acid sold under the trademark Biolac TM which has a pH of 1.56 (Barnet Lot #8238) were added 4.14 grams of "sodium hydroxymethylglycinate sold under the trademark" Suttocide A ® which has a pH of 10.00 (Sutton Lot #1013330) and the mixture was stirred for 10 seconds. The results of this neutralization process were that the temperature of the mixture was increased by 2° C. (from 28° to 30° C.) and the pH of the mixture at the end was 5.43.

LEMON/PASSION FRUIT TM BRAND TRIPLE ALPHA HYDROXY ACID COMPLEX NEUTRALIZATION:

To 3.60 grams "triple alpha hydroxy acid complex sold under the trademark" Lemon/Passion Fruit Complex TM which has a pH of 1.28 (Centerchem Lot #320201) were added 4.52 grams "sodium hydroxymethylglycinate sold under the trademark" Suttocide A ® which has a pH of 10.00 (Lot #1013330) and the mixture was stirred for 10 seconds. The results of this neutralization process were that the temperature of the mixture was increased by 2° C. (from 28° to 30° C.) and the pH of the mixture at the end was 5.03.

The temperature increase and the pH increase involved in the neutralization experiments conducted according to Example 5 may be caused by one of two mechanisms. The most likely possibility is that a neutralization reaction is taking place in which the lactic acid is neutralizing the amine function of the hydroxymethylglycinate. The other possibility is the formation of a charge transfer complex, which is an extremely stable association between two molecules caused by multiple hydrogen or other non-covalent bonds.

It is understood that the present invention can take many forms and embodiments. The embodiments described herein are intended to illustrate rather than to limit the invention, it being appreciated that variations may be made without departing from the spirit or the scope of the invention.

Although illustrative embodiments of the invention have been described, a wide range of modification, change and substitution is intended in the foregoing disclosure and in some instances some features of the present invention may be employed without a corresponding use of the other features. Accordingly, it is appropriate that the appended claims be construed broadly and in a manner consistent with the scope of the invention.

What is claimed is:

1. A topical skin cream composition, comprising:
   a) from about 0.05% to about 15.00% by weight of an alpha hydroxy acid complex comprising citric acid, lactic acid and tartaric acid;
   b) from about 0.01% to about 15.00% by weight of a composition comprising about 28.00% to about 35.00% by weight of lactic acid;
   c) from about 0.20% to about 1.50% by weight of sodium hydroxymethylglycinate; and
   d) a diluent or carrier for the composition comprising one or more compounds selected from the group consisting of water, suspending agents, thickeners humectants, preservatives, emollients, emulsifiers, film formers and fragrant oils.

2. A topical skin cream composition according to claim 1, wherein said diluent or carrier comprises:
   a) a suspending agent comprising between about 0.20% and 2.00% by weight of magnesium aluminum silicate;
   b) at least one thickener comprising between about 0.05% and 0.50% by weight of hydroxyethylcellulose, between about 0.01% and 0.70% by weight of xanthan gum and between about 0.50% and 5.00% by weight of stearyl alcohol;
   c) a humectant comprising between about 1.00% to about 8.00% by weight of propylene glycol;
   d) at least one preservative comprising between about 0 01% to 0.50% by weight of phenoxyethanol and between about 0.01% to 1.00% by weight of benzyl alcohol;
   e) at least one emollient comprising between about 1.00% and 12.00% by weight of caprylic/capric triglyceride, between about 1.00% and 10.00% by weight of isopropyl palmitate, between about 0.10% and 4.00% by weight of dimethicone, between about 1.00% and 6.00% by weight of a saturated branched chain hydrocarbon obtained by hydrogenation of shark liver oil or other natural oils and between about 1.00% and 6.00% by weight of cyclic dimethyl polysiloxane;
   f) at least one emulsifier comprising between about 1.00% and 10.00% by weight of stearic acid, between about 2.50% and 10.00% by weight of glyceryl stearate/polyethylene glycol 100 stearate, between about 0.20% and 4.00% by weight of cetyl alcohol, between about 0.20% and 2.00% by weight of sorbitan stearate and between about 0.50% and 9.00% by weight of stearyl alcohol and ceteareth-20;
   g) a film former comprising between about 1.00% and 5.00% by weight of a mixture of liquid hydroxyl terminated polymers and polyethylene glycol;
   h) at least one fragrant oil comprising between about 0.01% and 0.30% by weight of almond oil and between about 0.01% and 0.50% by weight of jasmine oil; and
   i) water forming the balance.

3. A topical skin cream composition according to claim 1, wherein said diluent or carrier comprises:
   a) a suspending agent comprising between about 0.20% and 2.00% by weight of magnesium aluminum silicate;
   b) a thickener comprising between about 0.05% and 0.50% by weight of hydroxyethylcellulose;
   c) a humectant comprising between about 1.00% to about 8.00% by weight of propylene glycol;
   d) at least one preservative comprising between about 0.01% to 0.50% by weight of phenoxyethanol and between about 0.01% to 1.00% by weight of benzyl alcohol;
   e) at least one emollient comprising between about 1.00% and 12.00% by weight of caprylic/capric triglyceride, between about 1.00% and 10.00% by weight of isopropyl palmitate and between about 0.10% and 4.00% by weight of dimethicone;

f) at least one emulsifier comprising between about 1.00% and 10.00% by weight of stearic acid, between about 2.50% and 10.00% by weight of glyceryl stearate/polyethylene glycol 100 stearate, between about 0.20% and 4.00% by weight of cetyl alcohol and between about 0.20% and 2.00% by weight of sorbitan stearate;

g) at least one fragrant oil comprising between about 0.01% and 0.30% by weight of almond oil and between about 0.01% and 0.50% by weight of jasmine oil; and h) water forming the balance.

4. A topical skin cream composition according to claim 1, comprising:

0.10% by weight of said alpha hydroxy acid complex comprising citric acid, lactic acid and tartaric acid; 10.00% by weight of said composition comprising about 28.00% to about 35.00% by weight of lactic acid; 0.75% by weight of said sodium hydroxymethylglycinate; 0.80% by weight of said magnesium aluminum silicate; 0.20% by weight of said hydroxyethylcellulose; 8.00% by weight of said propylene glycol; 0.30% by weight of said phenoxyethanol; 0.50% by weight of said benzyl alcohol; 8.00% by weight of said caprylic/capric triglyceride; 5.80% by weight of said isopropyl palmitate; 1.30% by weight of said dimethicone; 5.00% by weight of said stearic acid; 7.00% by weight of said glyceryl stearate/polyethylene glycol 100 stearate; 0.60% by weight of said cetyl alcohol; 0.50% by weight of said sorbitan stearate; 0.03% by weight of said almond oil; 0.03% by weight of said jasmine oil; and 54.09% of said deionized water.

5. A topical skin cream composition according to claim 1, comprising:

10.00% by weight of said alpha hydroxy acid complex comprising citric acid, lactic acid and tartaric acid;

0.75% by weight of said sodium hydroxymethylglycinate; 0.80% by weight of said magnesium aluminum silicate; 0.20% by weight of said hydroxyethylcellulose; 5.00% by weight of said propylene glycol; 0.30% by weight of said phenoxyethanol; 0.50% by weight of said benzyl alcohol; 8.00% by weight of said caprylic/capric triglyceride; 5.00% by weight of said isopropyl palmitate; 1.00% by weight of said dimethicone; 6.00% by weight of said stearic acid; 7.00% by weight of said glyceryl stearate/polyethylene glycol 100 stearate; 0.80% by weight of said cetyl alcohol; 0.50% by weight of said sorbitan stearate; 0.03% by weight of said almond oil; 0.03% by weight of said jasmine oil; and 54.09% of said deionized water.

* * * * *

UNITED STATES PATENT AND TRADEMARK OFFICE
CERTIFICATE OF CORRECTION

PATENT NO. : 5,407,958

DATED : APRIL 18, 1995

INVENTOR(S) : Jinger L. Heath, et al.

It is certified that error appears in the above-identified patent and that said Letters Patent is hereby corrected as shown below:

Column 3, line 4, U.S. Patent should be --U.S.P.--
Column 3, line 7, U.S. Patent should be --USP--

Column 4, line 54, "alocohol" should be --alcohol--.
Column 4, line 66, "propeller-type sold under the trademark Lightnin$^{tm}$ mixer" should be --propeller-type mixer sold under the trademark Lightnin$^{tm}$--.
Column 8, line 28, "14" should be --24--.
Column 8, line 53, "propeller-type sold under the trademark Lightnin$^{tm}$ mixer" should be --propeller-type mixer sold under the trademark Lightnin$^{tm}$
Column 9, line 9, "BRANK" should be --BRAND--

Signed and Sealed this

Seventeenth Day of October, 1995

*Attest:*

BRUCE LEHMAN

*Attesting Officer*     *Commissioner of Patents and Trademarks*